United States Patent
Miles et al.

(10) Patent No.: US 6,732,591 B2
(45) Date of Patent: May 11, 2004

(54) DEVICE AND METHOD FOR FATIGUE TESTING OF MATERIALS

(75) Inventors: Toby J Miles, Sutton Coldfield (GB); Gerald Deshais, Derby (GB); Robin J Williams, Derby (GB); Martin McElhone, Derby (GB)

(73) Assignee: Rolls-Royce plc, London (GB)

( * ) Notice: Subject to any disclaimer, the term of this patent is extended or adjusted under 35 U.S.C. 154(b) by 0 days.

(21) Appl. No.: 09/922,087

(22) Filed: Aug. 6, 2001

(65) Prior Publication Data

US 2002/0017144 A1 Feb. 14, 2002

(30) Foreign Application Priority Data

Aug. 9, 2000 (GB) .............................................. 0019434

(51) Int. Cl.$^7$ ................................................. G01N 3/32
(52) U.S. Cl. ....................................................... 73/808
(58) Field of Search .......................... 73/808, 797, 798, 73/856, 860, 857, 796, 606, 799, 811, 862.69, 794, 855, 862.17, 790, 817, 849; 600/415

(56) References Cited

U.S. PATENT DOCUMENTS

| | | | |
|---|---|---|---|
| 4,112,746 A | * | 9/1978 | Itoh et al. ........................ 73/95 |
| 4,478,086 A | * | 10/1984 | Gram ........................... 73/781 |
| 5,079,955 A | * | 1/1992 | Eberhardt ..................... 73/799 |
| 5,719,339 A | * | 2/1998 | Hartman et al. ............... 73/811 |
| 5,758,970 A | | 6/1998 | Aubert |
| 5,877,432 A | * | 3/1999 | Hartman et al. .......... 73/862.69 |
| 5,883,311 A | * | 3/1999 | Hettiarachchi et al. ....... 73/799 |
| 5,952,581 A | * | 9/1999 | Lammers et al. ............. 73/831 |
| 6,023,980 A | * | 2/2000 | Owen et al. .................. 73/797 |

FOREIGN PATENT DOCUMENTS

| | | |
|---|---|---|
| EP | 0094486 A | 11/1983 |
| EP | 0175257 A | 3/1986 |
| FR | 2680003 A | 2/1993 |
| GB | 2060179 A | 4/1981 |
| GB | 2161936 A | 1/1986 |

* cited by examiner

*Primary Examiner*—Edward Lefkowitz
*Assistant Examiner*—Octavia Davis
(74) *Attorney, Agent, or Firm*—W. Warren Taltavull; Manelli, Denison & Selter PLLC

(57) ABSTRACT

A device (10) for fatigue testing of materials comprises a frame (14), first and second clamping means (16,18) for holding a specimen (12) to be tested. First and second mounting means (20,22) mount the clamping means (16,18) on the frame (14). The mounting means (20,22) vibrationally isolate the clamping means (16,18) from the frame (14). Actuator means (24) moves the first clamping means (16) relative to the second clamping means (18) to apply a low cycle load on the specimen (12). Electrical insulating means (30) electrically insulate the frame (14) from the specimen (12). A shaker (26) is coupled to the second clamping means (18) to apply a high cycle load on the specimen (12). A detector (32) detects the vibration of the specimen (12) and sends an electrical signal to a control unit (42) which determines the resonant frequency of the specimen (12). The control unit (42) sends a signal to the shaker (26) to maintain the high cycle load at the resonant frequency of the specimen (12). Electrical potential drop probes (38) are provided on the specimen (12) to send a second electrical signal to the control unit (42) which is arranged to determine the rate of crack growth, the fatigue life to crack initiation and fatigue life to failure of the specimen (12).

34 Claims, 2 Drawing Sheets

DEVICE AND METHOD FOR FATIGUE TESTING OF MATERIALS

FIELD OF THE INVENTION

The present invention relates to a device and method for fatigue testing of materials and in particular relates to a device and method for combined low cycle fatigue and high cycle fatigue testing of materials.

BACKGROUND OF THE INVENTION

Gas turbine engine fan blades, compressor blades and turbine blades are subjected to a combination of low cycle fatigue and high cycle fatigue stresses in operation of the gas turbine engine. These low cycle fatigue and high cycle fatigue stresses have a detrimental effect on the integrity of the fan blades, compressor blades and turbine blades. The low cycle fatigue (LCF) is a result of the centrifugal force experienced by the fan blades, compressor blades and turbine blades as they rotate about the axis of the gas turbine engine. The high cycle fatigue (HCF) is a result of aerodynamic and other vibration excitation of the fan blades, compressor blades and turbine blades.

The centrifugal force on a fan blade may exert a mean stress of the order of 500 MPa, or more, resulting in low cycle fatigue. The high cycle fatigue fundamental mode frequencies may vary from about 50 Hz for a fan blade to several kHz, for example 2 to 3 kHz, for a high-pressure compressor blade.

The high cycle fatigue damage quickly builds up due to the relatively large number of cycles in relatively short periods of time. The damaging effect of the mechanical cycles is exacerbated by the thermal cycles to which the gas turbine engine is subjected in operation.

In order to design fan blades, compressor blades and turbine blades which are resistant to fatigue, a good understanding of the combination of the steady and alternating stresses a blade may tolerate for any vibration mode that may be excited in operation is required.

The fatigue testing of materials under conditions representative of gas turbine engine operating conditions is difficult to achieve for blade aerofoil shapes and blade root shapes. Conventional low cycle (LCF), high cycle fatigue (HCF) and fatigue crack growth (FCC) have been used to provide mechanical data on simple specimen shapes. Direct comparison between simple specimen shapes and real blades have revealed marked differences in fatigue life. Consequently safety factors, typically 50%, are commonly applied to the fatigue data.

Thus there is a requirement to produce fatigue testing data from specimens whose geometry and state of stress is comparable to real blades in order to aid the design of blades resistant to fatigue or to more accurately determine the working life of real blades.

SUMMARY OF THE INVENTION

Accordingly the present invention seeks to provide a novel device for fatigue testing of materials which reduces, preferably overcomes, the above mentioned problems.

Accordingly the present invention provides a device for fatigue testing of materials comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in operation a low cycle load on the specimen, means to measure the low cycle load, vibration excitation means acoustically coupled to one of the first and second clamping means to apply in operation a high cycle load on the specimen, means to measure the high cycle load, detector means to detect vibration of the specimen and to produce an electrical signal, control means arranged to receive the electrical signal, the control means determining the resonant frequency of the specimen from the electrical signal and sending a signal to the vibration excitation means to maintain the high cycle load at the resonant frequency of the specimen and means to store data of the test.

Preferably the mounting means comprises first leaf spring to mount the first clamping means and a second leaf spring to mount the second clamping means.

Preferably the resonant frequency of the mounting means and first and second clamping means is arranged to be lower than the resonant frequency of the specimen.

Preferably the vibration excitation means comprises an actuator.

Preferably the actuator is arranged to generate frequencies in the range 50 Hz to 5 kHz.

Preferably the actuator is acoustically coupled to the first or second clamping means via a drive rod.

Preferably the actuator is an electrodynamic, piezoelectric or a magnetostrictive actuator.

Preferably there are heating means to heat the specimen.

Preferably the heating means comprises a furnace arranged to surround the specimen.

Preferably electrical insulating means electrically insulate the frame from the specimen.

Preferably there are means to supply an electrical current through the specimen, probes arranged on opposite sides of a crack on the specimen to produce a second electrical signal, means to determine crack growth rate arranged to receive the second electrical signal and to determine the rate of crack growth in the specimen.

Preferably the means to store data stores the life of the specimen to the initiation of the first crack.

Preferably the means to store data stores the life of the specimen to failure

The present invention also provides a method of fatigue testing of materials using a device comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in operation a low cycle load on the specimen, means to measure the low cycle load, electrical insulating means electrically insulate the frame from the specimen, vibration excitation means acoustically coupled to one of the first and second clamping means to apply in operation a high cycle load on the specimen, means to measure the high cycle load, detector means to detect vibration of the specimen and to produce an electrical signal, control means arranged to receive the electrical signal, the control means determining the resonant frequency of the specimen from the electrical signal and sending a signal to the vibration excitation means to maintain the high cycle load at the resonant frequency of the specimen and means to store data of the test, the method comprising (a) applying a low cycle load and/or a high cycle load to the specimen, (b) maintaining the vibration of the specimen at its resonant frequency, (c) detecting a drop in the resonant frequency of the specimen indicative of the initiation of a crack in the specimen, (d) stopping the test and locating the crack, (e) attaching probes to the specimen at each side of the crack, the probes are arranged to produce a second electrical signal, (f) supplying an electrical current through the specimen, (g) resuming the test and maintaining the vibration of the specimen at its resonant frequency until failure of the specimen occurs, (h) determining the rate of crack growth in the specimen from the second electrical signal and/or determining the life of the specimen to failure.

The method may comprise applying tensile load and bending mode vibrations on the specimen.

The method may comprise applying tensile load and torsion mode vibrations on the specimen.

The specimen may be aerofoil shaped.

The method may comprise heating the specimen.

The method may comprise determining the life of the specimen to the initiation of the first crack.

Step (d) may comprise heating the specimen to oxidise and color the surfaces of the crack on the specimen.

Step (b) may comprise maintaining the vibration of the specimen at a predetermined amplitude of vibration.

The method may comprise determining the amount of energy required to vibrate the specimen at the predetermined amplitude of vibrations at the resonant frequency of the specimen.

Preferably the specimen comprises a damping treatment or a damping coating.

The present invention also provides a device for fatigue testing of materials comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in operation a low cycle load on the specimen, means to measure the low cycle load, electrical insulating means to electrically insulate the frame from the specimen, vibration excitation means acoustically coupled to one of the first and second clamping means to apply in operation a high cycle load on the specimen, means to measure the high cycle load, detector means to detect vibration of the specimen and to produce an electrical signal, control means arranged to receive the electrical signal, the control means determining the resonant frequency of the specimen from the electrical signal and sending a signal to the vibration excitation means to maintain the high cycle load at the resonant frequency of the specimen, probes being provided on the specimen in operation and being arranged to produce a second electrical signal, means to supply an electrical current through the specimen, means to determine crack growth rate arranged to receive the second electrical signal and to determine the rate of crack growth in the specimen and/or determining the life of the specimen to failure.

Preferably there may be means to heat the specimen to oxidise and color the surfaces of the crack on the specimen. The control means may determine the amplitude of vibration of the specimen from the electrical signal and sends a signal to the vibration excitation means to maintain the high cycle load at a predetermined amplitude of vibration. The control unit may determine the amount of energy required to vibrate the specimen at the predetermined amplitude of vibration at the resonant frequency of the specimen. The specimen may comprise a damping treatment or a damping coating.

BRIEF DESCRIPTION OF THE INVENTION

The present invention will be more fully described by way of example with reference to the accompanying drawings in which.

DETAILED DESCRIPTION OF THE INVENTION

Figure 1:
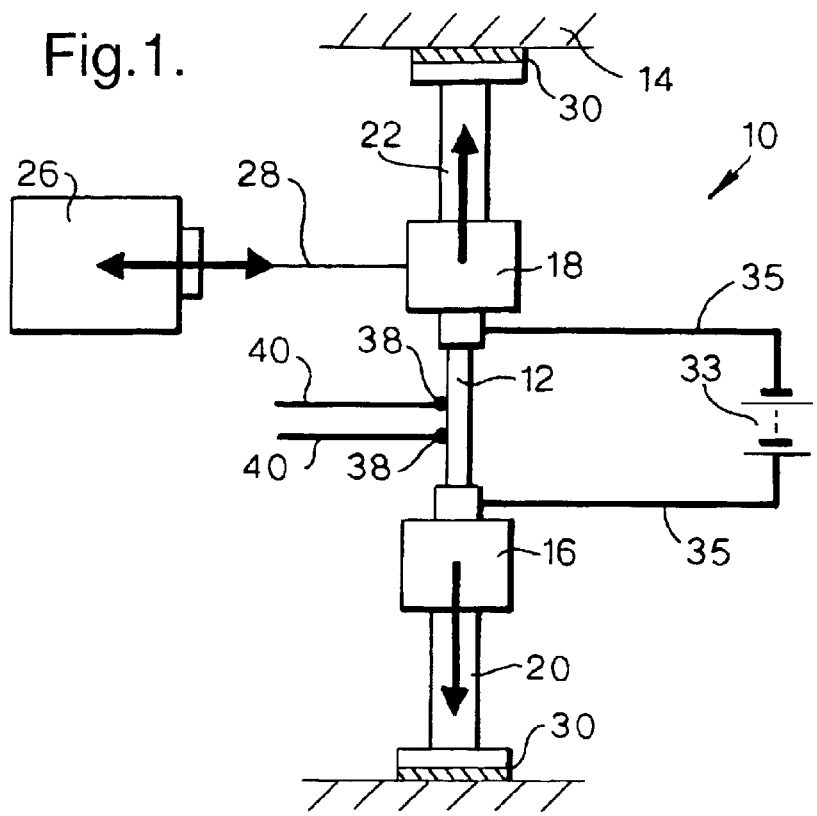
FIG. 1 shows a device for fatigue testing of materials according to the present invention.
Figure 2:
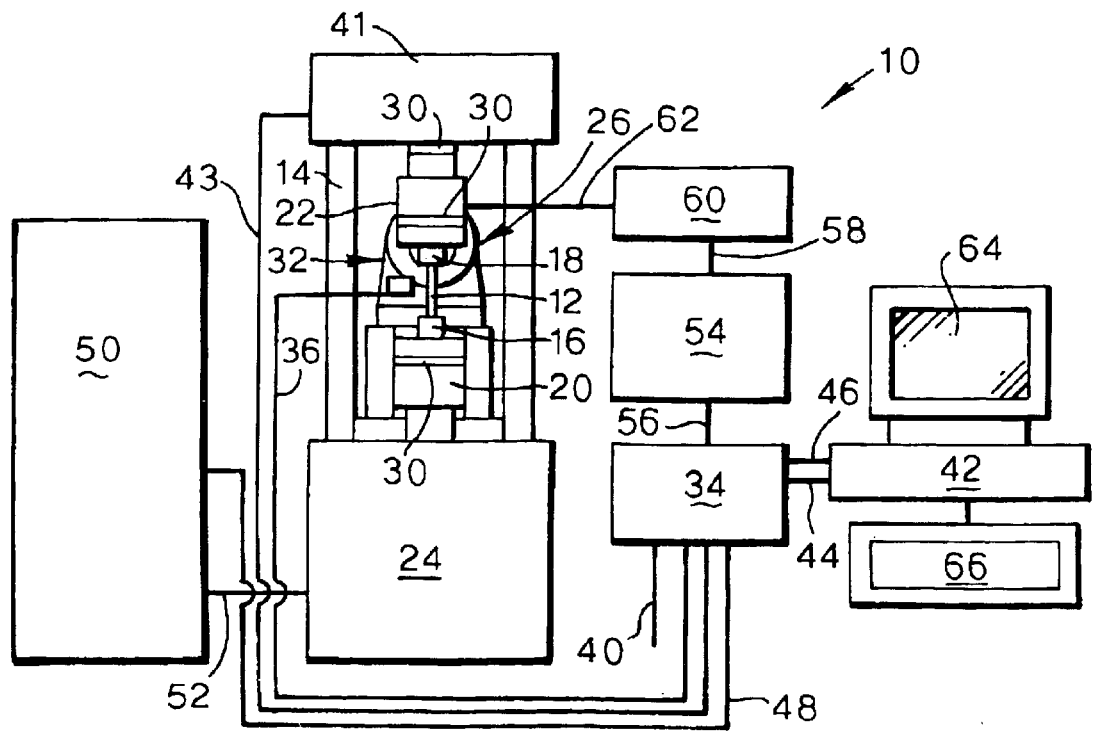
FIG. 2 is a schematic diagram of the device for fatigue testing of materials shown in FIG. 1.
Figure 3:
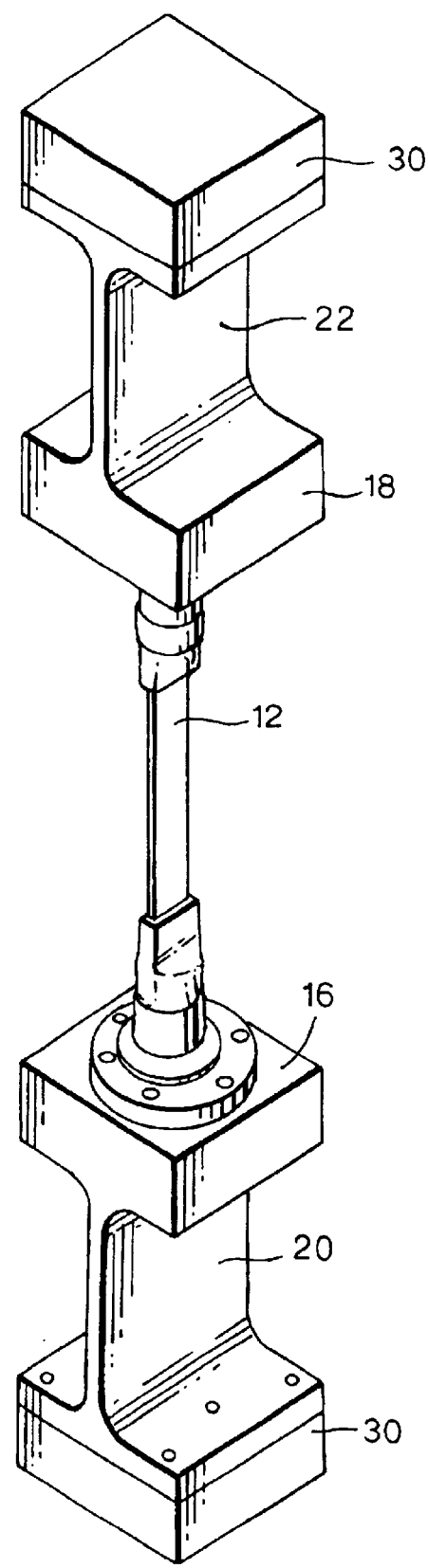
FIG. 3 shows a perspective view of a portion of the device shown in FIG. 1.

A device 10 for fatigue testing of materials is shown in FIGS. 1 to 3. The device 10 for fatigue testing of materials, for example a specimen 12, comprises a frame 14, first clamping means 16, second clamping means 18, first mounting means 20 and second mounting means 22. The first and second clamping means 16 and 18 hold opposite longitudinal ends of the specimen 12. The first and second clamping means 16 and 18 and the ends of the specimen 12 have co-operating features to allow the first and second clamping means 16 and 18 to grip the specimen 12. The co-operating features for example may be threaded apertures in the first and second clamping means 16 and 18 and threaded ends of the specimen 12 or alternatively dovetail or firtree connections. The first and second clamping means 16 and 18 have a relatively large mass and rotational inertia and act substantially, or approximately, as nodal points during vibration of the specimen 12 in its bending modes.

The first and second mounting means 20 and 22 mount the first and second clamping means 16 and 18 on the frame 14. The first and second mounting means 20 and 22 vibrationally isolate the first and second clamping means 16 and 18 from the frame 14. The first and second mounting means 20 and 22 for example comprise leaf springs, which are shown more fully in FIG. 3. The leaf springs are much wider than they are thick. The resonant frequency of the first and second clamping means 16 and 18 and the first and second mounting means 20 and 22 is arranged to be lower than the resonant than the resonant frequency of the specimen 12.

The leaf springs 20 and 22 may be connected to the frame 14 by a solid connection or by a resilient connection to minimise the transmission of bending moments to the frame 14. The resilient connection may comprise further leaf springs.

An actuator 24 is provided to move the first and second clamping means 16 and 18 relative to each other. In this example the actuator 24 is arranged to move the first clamping means 16 and first mounting means 20 relative to the second clamping means 18, the second mounting means 22 and the frame 14 to apply in operation a low cycle load on the specimen 12. The low cycle load may be either a tension load or a compression load. The actuator 24 may be an electromechanical screw drive, an electric motor, hydraulic piston or any other suitable actuator. The actuator 24 may apply loads up to 100 kN or greater.

A shaker 26, or actuator, is acoustically coupled to one of the first and second clamping means 16 and 18. In this example the shaker 26 is acoustically coupled to the second clamping means 18, by a drive member 28 for example a drive rod and/or an excitation spring, to apply in operation a high cycle load on the specimen 12. The actuator 26 may be an electrodynamic, a piezoelectric or a magnetostrictive actuator. The actuator 26 is arranged to produce vibrations in the frequency range 50 Hz to 5 kHz. The leaf springs of the first and second mounting means 20 and 22 are arranged such that the width of the leaf springs extends transversely to the direction in which the shaker 26 applies the load on the specimen 12. The stiffness of the drive member 28 is selected so that the mass of the shaker 26 and the drive member 28 have a natural resonant frequency close to the bending mode of the specimen 12.

One or more electrical insulators 30 are provided to electrically insulate the frame 14 from the specimen 12. The electrical insulators 30 are provided between the first mounting means 20 and the actuator 24 and between the second mounting means 22 and the frame 14. The electrical insulator 30 comprises any suitable material which prevents the flow of an electrical current. The first and second mounting means 20 and 22 are bolted to the actuator 24 and the frame 14 by electrically insulating bolts.

One or more detectors 32 are arranged to detect displacement, or vibration, of the specimen 12. The detectors 32 are proximity probes, accelerometers or optical displacement probes. The detectors 32 are electrically connected to a data input and control signal output unit 34 by electrical connectors 36.

A stabilised electrical power supply 33 is electrically connected to the opposite ends of the specimen 12 by electrical connectors 35. The power supply 33 is arranged to supply a current of 50 to 100 A through the specimen 12. The power supply 33 is arranged to supply a DC current which is pulsed periodically to prevent heating of the specimen. Alternatively the power supply 33 is arranged to supply an AC current which prevents heating of the specimen 12. A load cell 41 is provided on the frame 14 to measure the mean axial stress on the specimen 12. The load cell 41 is electrically connected to the data input and control signal output unit 34 by electrical connectors 43.

During testing electrical potential drop probes 38 are welded to the specimen 12 on each side of a crack. The potential drop probes 38 are electrically connected to the data input and control signal output unit 34 by electrical connectors 40.

The data input and control signal output unit 34 supplies the electrical signals from the detectors 32, the probes 38 and the load cell 41 to a main control unit 42 by an electrical connector 44.

The main control unit 42 supplies control signals to a control unit 50 for the actuator 24 through an electrical connector 46, the data input and control signal output unit 34 and an electrical connector 48. The control unit 50 supplies control signals to the actuator 24 through an electrical connector 52.

The main control unit 42 supplies control signals to a waveform generator 54 for the shaker 26 through the electrical connector 46, the data input and control signal output unit 34 and an electrical connector 56. The waveform generator 54 is connected to the shaker 26 through an electrical connector 58, a power amplifier 60 and an electrical connector 62.

The main control unit 42 comprises for example a personal computer or a computer. The main control unit 42 is arranged to store data and is connected to a monitor 64 and a printer 66.

The main control unit 42 is arranged to analyse the electrical signals from the detectors 32 to determine the resonant frequency of vibration of the specimen 12. The main control unit 42 has simulated test data and a relationship to determine the high cycle fatigue stresses/loads applied to the specimen 12 from the measure of displacement provided by the detectors 32. The main control unit 42 is arranged to analyse the electrical signals from the probes 38 to determine the electrical potential drop across a crack in the specimen 12.

The specimen 12 is enclosed in a furnace, not shown, to heat the specimen 12 to a higher temperature representative of the temperature of operation of a real component. The furnace is arranged to heat the specimen up to any suitable temperature, for example up to 700° C. or higher.

The main control unit 42 is also connected to the control unit of the furnace to maintain the specimen 12 at a predetermined temperature.

In operation to fatigue test a specimen 12 the ends of a specimen 12 to be tested are placed in the first and second clamping means 16 and 18. The specimen 12 substantially reproduces geometric features found on a real component, for example a gas turbine engine fan blade, compressor blade or turbine blade and is manufactured from the same material, for example the same alloy. The specimen 12 shown reproduces the fillet radius connection between the aerofoil and a platform of compressor blade.

The main control unit 42 sends electrical signals to the control unit for the furnace to heat the specimen 12 to a predetermined temperature or to maintain the specimen 12 at ambient temperature.

The main control unit 42 sends electrical signals to the control unit 50 and the waveform generator 54 to apply low cycle loads, high cycle loads or a combination of low cycle loads and high cycle loads on the specimen 12.

The detectors 32 send electrical signals corresponding to the amplitude and frequency of vibration of the specimen 12 to the main control unit 42. The main control unit 42 analyses the electrical signals and determines the resonant frequency of the specimen 12. The main control unit 42 then sends further electrical signals to the control unit 50 and/or the waveform generator 54 to maintain the frequency of vibration of the specimen 12 at its resonant frequency to generate a crack in the specimen 12.

The main control unit 42 continues to analyse the electrical signals from the detectors 32 to determine if a crack has been generated in the specimen 12. The main control unit 42 determines that a crack has been generated in the specimen 12 when the resonant frequency of the specimen drops to a lower frequency. Once a crack has been generated in the specimen 12 the main control unit 42 stops the fatigue test and the position of the crack in the specimen 12 is determined.

The position of the crack in the specimen 12 is determined by for example applying a dye to the surface of the specimen 12 and then removing the dye. The specimen 12 is inspected visually to find remains of the dye in the crack and hence the position of the crack in the specimen 12. Alternatively other methods of determining the position of the crack may be used.

The potential drop probes 38 are welded to the specimen 12 on the opposite sides of the crack.

The fatigue test is restarted and the main control unit 42 again sends electrical signals to the control unit 50 and/or the waveform generator 54 to maintain the frequency of vibration of the specimen 12 at its resonant frequency. The main control unit 42 may maintain the frequency of vibration at the resonant frequency even during changes in the resonant frequency of the specimen 12 due to growth of the crack, until the specimen 12 fractures. Alternatively the main control unit 42 may not maintain the frequency of vibration at the resonant frequency of the specimen 12.

The main control unit 42 analyses the electrical signals from the potential drop probes 38 to determine the rate of crack growth in the specimen 12. The main control unit 42 is arranged to store the data and/or display the data on the monitor 64 and/or on the printer 66.

The main control unit 42 is arranged to determine and store the low cycle loads and the high cycle loads applied to the specimen 12 over time and thus produce a history of the loads applied to the specimen 12. The load history may include the number of cycles to failure of the specimen 12 and/or the number of cycles to the start of a crack in the specimen 12. The load history may include the magnitude of the loads and the frequency of the vibrations. The main control unit 42 is arranged to display the data on the monitor 64 and/or on the printer 66.

In a further method of operation to fatigue test a specimen 12, the same procedure is followed until a crack has been generated in the specimen 12 and the main control unit 42 stops the fatigue test. The specimen 12 is removed from the fatigue testing device 10 and is heated at a high temperature for a short period of time to oxidise and color the fracture surfaces of the specimen 12.

The specimen 12 is placed into the fatigue testing device 10 and the potential drop probes 38 may or may not be welded to the specimen 12. The fatigue test is started and the main control unit 42 again sends signals to the control unit 50 and/or waveform generator 54 to maintain the frequency of vibration of the specimen 12 at its resonant frequency until the specimen 12 fractures or fails completely. The fracture surfaces of the specimen 12 are analysed to enable accurate modelling of crack formation and to distinguish crack initiation from crack propagation. The oxidised and colored fracture surfaces are those formed during crack initiation and the unoxidised and colored uncolored fracture surfaces are those formed during crack growth/propagation.

The present invention also provides a device for fatigue testing of materials comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in operation a low cycle load on the specimen, means to measure the low cycle load, electrical insulating means to electrically insulate the frame from the specimen, vibration excitation means acoustically coupled to one of the first and second clamping means to apply in operation a high cycle load on the specimen, means to measure the high cycle load, detector means to detect vibration of the specimen and to produce an electrical signal, control means arranged to receive the electrical signal, the control means determining the resonant frequency of the specimen from the electrical signal and sending a signal to the vibration excitation means to maintain the high cycle load at the resonant frequency of the specimen, probes being provided on the specimen in operation and being arranged to produce a second electrical signal, means to supply an electrical current through the specimen, means to determine crack growth rate arranged to receive the second electrical signal and to determine the rate of crack growth in the specimen and/or determining the life of the specimen to failure.

The low cycle load applied may be a tensile load or a compressive load. The high cycle load may be a torsion load or a bending load. The leaf springs of the mounting means may be redesigned to have low torsional stiffness to allow testing of the torsional modes of the specimen. A torsional load is applied by adjusting the position of the shaker. In this case the shaker is mounted off axis to apply a load to the second clamping means and a second shaker may be used to cancel the direct load applied to the second clamping means.

It may also be possible to put strain gauges on the specimen and relate the strain to the stress. This is more accurate but more expensive than using a load cell. It may be possible to locate one or more strain gauges at the axial mid point of the specimen and one ore or more strain gauges near the point where the specimen is going to fail. The exact positioning of the strain gauges depends on the geometry of the specimen.

The advantages of the invention are that it is able to fatigue test specimens which simulate the shape of real components under conditions experienced by real components. The ability to measure the rate of crack growth under low cycle load and high cycle load conditions and at elevated temperature is very important because the combination of a tensile load and bending/torsion mode vibration closely simulates the stresses experienced by real components in operation. The invention also allows the study of the influence of foreign object damage on the propagation of cracks and the integrity of components. The invention provides fatigue and crack propagation data which was not previously available. The use of this data will enable improvements in the design of components due to a clearer understanding of the behaviour of components and the safety margins. The invention enables the testing of components with identical shapes but manufactured from different materials and/or different processes to determine the effect the different materials and/or different processes have on the life of the component. The invention allows a better estimation of component life, safe stress limits Although the invention has been described with reference to testing gas turbine engine blades it may be used for testing steam turbine blades or other components or articles or sub-elements of components or articles.

We claim:

1. A device for fatigue testing of materials comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in use a low cycle load on the specimen in an axial direction, means to measure the low cycle load, vibration excitation means acoustically coupled to one of the first and second clamping means to apply in use a high cycle load on the specimen, means to measure the high cycle load, detector means to detect vibration of the specimen and to produce an electrical signal, control means to receive the electrical signal, the control means determining the resonant frequency of the specimen from the electrical signal and sending a signal to the vibration excitation means to maintain the high cycle load at the resonant frequency of the specimen and means to store data of the test, said vibration excitation means comprising an actuator, said actuator being mechanically and acoustically coupled to one of the first and second clamping means through a drive member comprising and said actuator and said drive member being located to one side of the said one of the first and second clamping means to apply the high cycle load transversely to the low cycle load, said drive member having a stiffness, said stiffness of the drive member being such that the mass of the drive member and actuator have a natural resonant frequency close to the resonant frequency of the specimen.

2. A device as claimed in claim 1 wherein the mounting means comprises a first leaf spring to mount the first clamping means and a second leaf spring to mount the second clamping means.

3. A device as claimed in claim that 1 wherein the resonant frequency of the mounting means and first and second clamping means is arranged to be lower than the resonant frequency of the specimen.

4. A device as claimed in claim 1 wherein the actuator is arranged to generate frequencies in the range 15 hertz to 5 kHz.

5. A device is claimed in claim 1 wherein the actuator is an electrodynamic, piezoelectric or a magnetostrictive actuator.

6. A device as claimed in claim 1 wherein there are heating means to heat the specimen.

7. A device as claimed in claim 6 wherein the heating means comprises a furnace surrounding the specimen.

8. A device as claimed in claim 1 wherein electrical insulating means electrically insulate the frame from the specimen.

9. A device as claimed in claim 8 wherein there are means to supply an electrical current through the specimen, probes arranged on opposite sides of a crack on the specimen to produce a second electrical signal, means to determine crack growth rate arranged to receive the second electrical signal and to determine the rate of crack growth in the specimen.

10. A device as claimed in claim 1 wherein the means to store data stores the life of the specimen to the initiation of the first crack.

11. A device as claimed in claim 1 wherein the means to store data stores the life of the specimen to failure.

12. A method of fatigue testing of materials using a device comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in use a low cycle load on the specimen in an axial direction, means to measure in the low cycle load to, electrical insulating means to electrically insulate the frame from the specimen, vibration excitation means acoustically coupled to one of the first and second clamping means to apply in operation a high cycle load on the specimen, said vibration excitation means comprising an actuator, said actuator being mechanically and acoustically coupled to one of the first and second clamping means through a drive member and said actuator and said drive member being located to one side of the said one of the first and second clamping means to apply the high cycle load transversely to the low cycle load, said drive member having a stiffness, said stiffness of the drive member being such that the mass of the drive member and actuator have a natural resonant frequency close to the resonant frequency of the specimen, means to measure the high cycle load, detector means to detect vibration of the specimen and to produce an electrical signal, control means to receive the electrical signal, the control means determining the resonant frequency of the specimen from the electrical signal and sending a signal to the vibration excitation means to maintain the high cycle load at the resonant frequency of the specimen and means to store data of the test, the method comprising the steps of:

(a) applying one of a low cycle load and a high cycle load to the specimen, (b) maintaining the vibration of the specimen at its resonant frequency, (c) detecting a drop in the resonant frequency of the specimen indicative of the initiation of a crack in the specimen, (d) stopping the test and locating the crack, (e) attaching probes to the specimen at each side of the crack, the probes being arranged to produce a second electrical signal, (f) supplying an electrical current through the specimen, (g) resuming the test and maintaining the vibration of the specimen at its resonant frequency until failure of the specimen occurs, (h) determining one of the rate of crack growth in the specimen from the second electrical signal and determining the life of the specimen to failure.

13. A method as claimed in claim 12 comprising applying tensile load and bending mode vibrations on the specimen.

14. A method as claimed in claim 12 comprising applying tensile load and torsion mode vibrations on the specimen.

15. A method as claimed in claim 12 wherein the specimen is aerofoil shaped.

16. A method as claimed in claim 12 comprising heating the specimen.

17. A method as claimed in claim 12 wherein step (c) comprises determining the life of the specimen to the initiation of the first crack.

18. A method as claimed in claim 12 wherein step (d) comprises heating the specimen to oxidise and colour the surfaces of the crack on the specimen.

19. A method as claimed in claim 12 wherein step (b) comprises maintaining the vibration of the specimen at a predetermined amplitude of vibration.

20. A method as claimed in claim 19 comprising determining the amount of energy required to vibrate the specimen at the predetermined amplitude of vibrations at the resonant frequency of the specimen.

21. A method as claimed in claim 20 wherein the specimen comprises a damping treatment.

22. A device for fatigue testing of materials comprising a frame, first and second clamping means for holding a specimen to be tested, mounting means to mount the first and second clamping means on the frame, the mounting means vibrationally isolating the first and second clamping means from the frame, means to move at least one of the first and second clamping means to apply in use a low cycle load on the specimen, means to measure the low cycle load, electrical insulating means to electrically insulate the frame from the specimen, vibration excitation means acoustically coupled to one of the first and second clamping means to apply in operation a high cycle load on the specimen, said vibration excitation means comprising an actuator, said actuator being acoustically coupled to one of the first and second clamping means through a drive and said actuator and said drive member being located to one side of the said one of the first and second clamping means to apply the high cycle load transversely to the low cycle load, said drive member having a stiffness, said stiffness of the drive member being such that the mass of the drive member and actuator have a natural resonant frequency close to the resonant frequency of the specimen, means to measure the high cycle load, detector means to detect vibration of the specimen and to produce an electrical signal, control means arranged to receive the electrical signal, the control means determining the resonant frequency of the specimen from the electrical signal and sending a signal to the vibration excitation means to maintain the high cycle load at the resonant frequency of the specimen, probes being provided on the specimen in use and to produce a second electrical signal, means to supply an electrical current through the specimen, means to determine crack growth rate arranged to receive the second electrical signal and to determine the rate of crack growth in the specimen or determining the life of the specimen to failure.

23. A device as claimed in claim 22 wherein the mounting means comprises first leaf spring to mount the first clamping means and a second leaf spring to mount the second clamping means.

24. A device as claimed in claim 22 wherein the resonant frequency of the mounting means and first end second clamping means is arranged to be lower than the resonant frequency of the specimen.

25. A device as claimed in claim 22 wherein the actuator is arranged to generate frequencies in the range 50 Hz to 5 kHz.

26. A device as claimed in claim 22 wherein the actuator is an electrodynamic, piezoelectric or a magnetostrictive actuator.

27. A device as claimed in claim 22 wherein there are heating means to heat the specimen.

28. A device as claimed in claim 27 wherein the heating means comprises a furnace surrounding the specimen.

29. A device as claimed in claim 22 wherein the means to store data stores the life of the specimen to the initiation of the first crack.

30. A device as claimed in claim 22 wherein the means to store data stores the life of the specimen to failure.

31. A device as claimed in claim 22 wherein there are means to heat the specimen to oxidise and colour the surfaces of the crack on the specimen.

32. A device as claimed in claim 22 wherein the control means determines the amplitude of vibration of the specimen from the electrical signal and sends a signal to the vibration excitation means to maintain the high cycle load at a predetermined amplitude of vibration.

33. A device as claimed in claim 32 wherein the control unit determines the amount of energy required to vibrate the specimen at the predetermined amplitude of vibration at the resonant frequency of the specimen.

34. A device as claimed in claim 33 wherein the specimen comprises a damping treatment.

* * * * *